United States Patent [19]
Carson

[11] 4,296,261
[45] Oct. 20, 1981

[54] PROCESS FOR THE MANUFACTURE OF ETHANOL FROM ETHYLENE

[75] Inventor: Don B. Carson, Mt. Prospect, Ill.

[73] Assignee: UOP Inc., Des Plaines, Ill.

[21] Appl. No.: 157,773

[22] Filed: Jun. 9, 1980

[51] Int. Cl.³ ............................................ C07C 29/12
[52] U.S. Cl. .................................... 568/890; 568/888; 568/889
[58] Field of Search ........................ 568/888, 890, 889

[56] References Cited

U.S. PATENT DOCUMENTS

| | | | |
|---|---|---|---|
| 2,045,616 | 6/1936 | Sargent | 568/890 |
| 2,081,166 | 5/1937 | Brooks | 568/890 |
| 2,474,568 | 6/1949 | Bannon et al. | 568/890 |

FOREIGN PATENT DOCUMENTS 715483  9/1954  United Kingdom ................ 568/889

OTHER PUBLICATIONS

Horie et al., "Hydrocarbon Processing", vol. 49, Mar. 1970, pp. 119, 120.

Schrage et al., "J. Ind. & Eng. Chem.", vol. 42, 1950, pp. 2550-2553.

*Primary Examiner*—Joseph E. Evans
*Attorney, Agent, or Firm*—James R. Hoatson, Jr.; Robert W. Welch; William H. Page, II

[57] ABSTRACT

A process for the manufacture of $C_2$-$C_5$ alcohols from $C_2$-$C_5$ olefins by the indirect hydration method is disclosed. The process comprises the steps of (a) treating a $C_2$-$C_5$ olefin in an absorption zone in admixture with a $C_2$-$C_5$ alkyl hydrogen sulfate at conditions to form a $C_2$-$C_5$ dialkyl sulfate; (b) treating said dialkyl sulfate in a hydrolyzing zone in admixture with a measured amount of water at conditions effecting the partial hydrolysis of said dialkyl sulfate and the formation of a $C_2$-$C_5$ alkyl hydrogen sulfate and a $C_2$-$C_5$ alcohol; (c) separating the alcohol; and (d) recycling the alkyl hydrogen sulfate to said absorption zone, and treating said $C_2$-$C_5$ olefin in admixture therewith in accordance with step (a). The practice of this invention substantially obviates the formation of sulfuric acid and the required reconcentration thereof.

9 Claims, 1 Drawing Figure

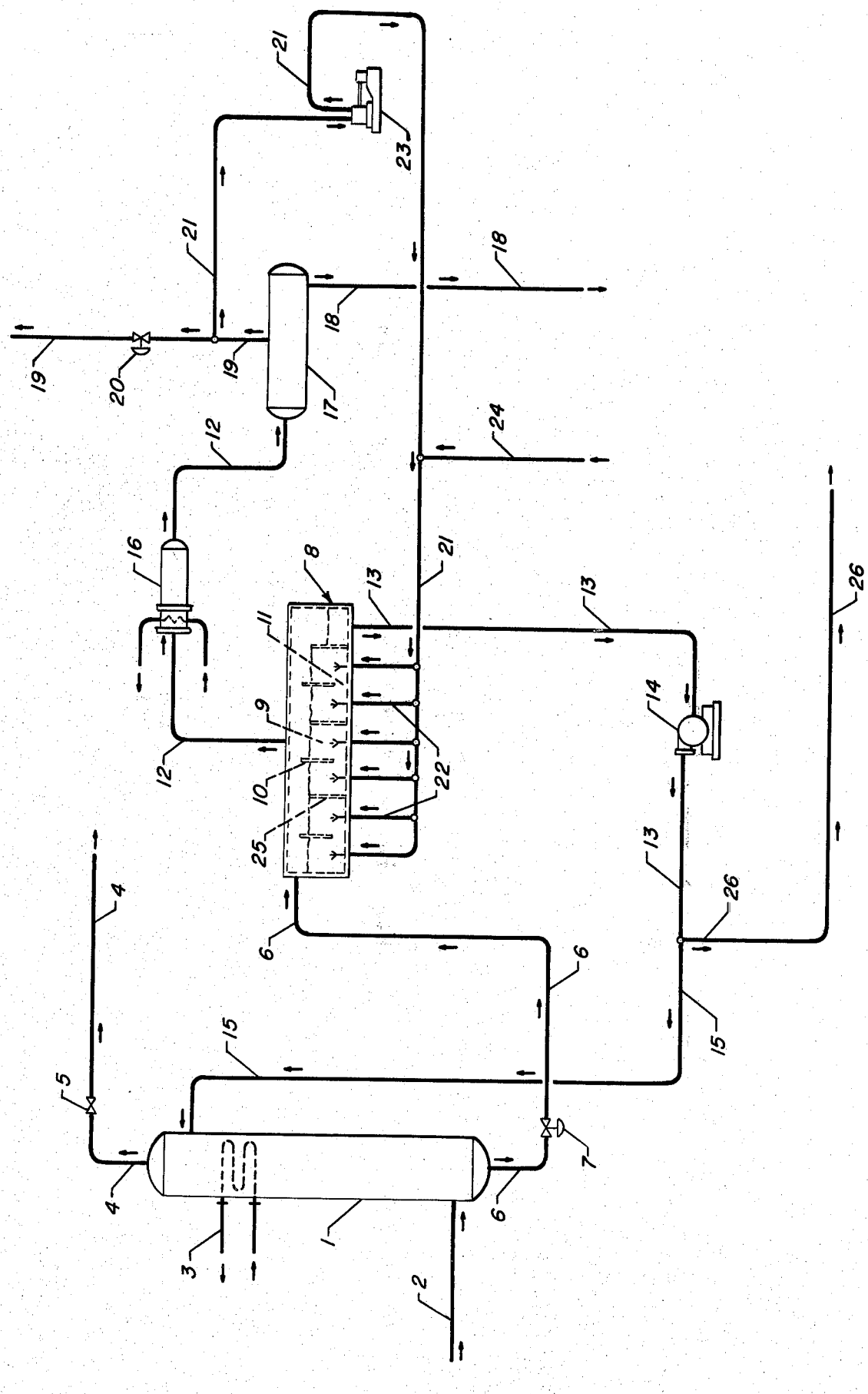

PROCESS FOR THE MANUFACTURE OF ETHANOL FROM ETHYLENE

This invention relates to the manufacture of $C_2$–$C_5$ alcohols from $C_2$–$C_5$ olefins by the indirect hydration process. More specifically, this invention relates to an improvement in the manufacture of ethanol from ethylene by the indirect hydration process whereby the recovery and reconcentration of sulfuric acid is obviated. The manufacture of ethanol from ethylene by the so-called indirect hydration or sulfuric acid route, wherein ethylene is initially absorbed in 95–100 wt.% sulfuric acid, is an old and well known process. The process is ordinarily operated in conjunction with a petroleum refinery where large volumes of ethylene-containing normally gaseous hydrocarbons are available, for example, as by-products of the steam, thermal or catalytic cracking of petroleum gas oil fractions. The ethylene-containing hydrocarbon feedstock is typically desulfurized and pretreated for the separation of the higher molecular weight olefins, taking advantage of the recognized preferential absorption of said olefins by the more dilute sulfuric acid solutions—e.g., 85 wt.% sulfuric acid. The resulting normally gaseous hydrocarbon stream is then treated in contact with 95–100 wt.% sulfuric acid whereby the ethylene is absorbed to form ethyl sulfates, and the non-absorbable saturated hydrocarbons, e.g., methane, ethane, propane, etc., and hydrogen, are discharged. The ethyl sulfates-containing sulfuric acid is subsequently diluted with water whereby the ethyl sulfates are hydrolyzed to ethanol. An important and costly part of the operation is in the recovery of the spent or diluted acid, and the reconcentration and recycle of the acid to the ethylene absorption phase of the process—the corrosive nature of sulfuric acid being well known.

It is therefore an object of this invention to present an improvement in the manufacture of ethanol from ethylene by the indirect hydration process whereby the recovery and reconcentration of sulfuric acid is obviated. It is a further object to minimize the amount of water to be removed from the ethyl sulfate hydrolysis product.

In one of its broad aspects, the present invention embodies a process for the manufacture of a $C_2$–$C_5$ alcohol which comprises the steps of (a) treating a $C_2$–$C_5$ olefin in an absorption zone in admixture with a $C_2$–$C_5$ alkyl hydrogen sulfate at conditions to form a $C_2$–$C_5$ dialkyl sulfate; (b) treating said dialkyl sulfate in a hydrolyzing zone in admixture with a measured amount of water at conditions effecting the partial hydrolysis of said dialkyl sulfate and the formation of a $C_2$–$C_5$ alkyl hydrogen sulfate and a $C_2$–$C_5$ alcohol; (c) separating said alcohol; and, (d) recycling the alkyl hydrogen sulfate to said absorption zone and treating said $C_2$–$C_5$ olefin in admixture therewith in accordance with step (a).

One of the more specific embodiments relates to a process for the manufacture of ethanol which comprises the steps of (a) treating ethylene in an absorption zone in admixture with ethyl hydrogen sulfate at a temperature of from about 70° to about 80° C. and at a pressure of from about 250 to about 350 psig.; (b) treating the resulting diethyl sulfate serially in a multiple-stage hydrolysis zone with a measured amount of water at a temperature of from about 50° to about 90° C., the water concentration in each of said stages being insufficient to hydrolyze all of the diethyl sulfate contained therein to ethyl hydrogen sulfate and ethanol, a substantial portion of said ethanol being stripped from each of said stages prior to further hydrolysis of said diethyl sulfate in ensuing stages; and, (c) recycling the ethyl hydrogen sulfate to said absorption zone and treating said ethylene in admixture therewith in accordance with step (a).

Other objects and embodiments of this invention will become apparent in the following detailed specification.

In accordance with the process of the present invention, a $C_2$–$C_5$ olefin is initially treated in an absorption column in admixture with a $C_2$–$C_5$ alkyl hydrogen sulfate. For example, ethylene is initially treated in an absorption column in admixture with ethyl hydrogen sulfate. While propylene, butylene and amylene, and especially propylene, are also absorbable in their corresponding alkyl hydrogen sulfates and converted to their respective alcohols by essentially the same process, albeit at somewhat milder conditions, the process of this invention is particularly directed to the manufacture of ethanol from ethylene, and the further description is presented with particular reference thereto.

In general, the $C_2$–$C_5$ olefin is admixed and absorbed in said alkyl hydrogen sulfate at a mole ratio of from about 0.1:1 to about 1:1. Reaction conditions relating to the formation of a dialkyl sulfate as herein contemplated, include a temperature of from about 60° to about 100° C. and a pressure of from about 100 to about 500 psig. Preferably, and particularly in the case of ethylene, said reaction conditions include a temperature of from about 70° to about 80° C. and a pressure of from about 200 to about 350 psig. Thus, in a preferred embodiment, ethylene is initially admixed and absorbed in ethyl hydrogen sulfate at a temperature of from about 70° to about 80° C. and at a pressure of from about 200 to about 350 psig.

The dialkyl sulfate, e.g., diethyl sulfate, resulting from the absorption of the $C_2$–$C_5$ olefin in the $C_2$–$C_5$ alkyl hydrogen sulfate, is subsequently hydrolyzed at conditions effecting the partial hydrolysis of said dialkyl sulfate and the formation of $C_2$–$C_5$ alcohol and $C_2$–$C_5$ alkyl hydrogen sulfate partial hydrolysis products. Thus, in a preferred embodiment, diethyl sulfate, resulting from the absorption of ethylene in ethyl hydrogen sulfate, is admixed with a measured amount of water at conditions effecting the partial hydrolysis of the diethyl sulfate and the formation of ethanol and ethyl hydrogen sulfate partial hydrolysis products. The measured amount of water is such as to minimize hydrolysis of the ethyl hydrogen sulfate and the consequent formation of sulfuric acid. Hydrolysis of the diethyl sulfate with water is somewhat complicated by the insolubility of the ester, and the hydrolysis operation is advantageously effected with a high degree of agitation. Reaction conditions relating to the partial hydrolysis operation include a temperature of from about 50° to about 90° C. and preferably from about 60° to about 85° C. Temperatures in excess of about 90° C. promote hydrolysis of the ethyl hydrogen sulfate with the formation of sulfuric acid, and said temperatures are to be avoided. The partial hydrolysis is suitably effected at about atmospheric pressure conditions. The alcohol product is advantageously stripped or otherwise separated from the hydrolysis reaction mixture substantially immediately as formed. This tends to preclude the formation of ether by-products, and to maintain the equilibrium of the hydrolysis reaction in favor of the production of alcohol. The hydrolysis operation is preferably effected in stages, the water charged to each stage being insufficient to achieve a partial hydrolysis of all of the diethyl sulfate contained therein. In the multiple stage hydrolysis operation, a substantial portion of the alcohol is withdrawn from each stage to promote the equilibrium hydrolysis reaction in the ensuing stages. In any case, the total amount of water charged to the multiple stage hydrolysis operation is less than required to partially hydrolyze all of the diethyl sulfate charged thereto; hence, little if any sulfuric acid is formed, and any that may form does not require reconcentration.

The further description of the process of this invention is presented with reference to the attached schematic drawing. The drawing represents one preferred embodiment of the invention and is not intended as an undue limitation on the generally broad scope of the invention as set out in the appended claims.

Referring then to the drawing, an off-gas from a fluid catalytic cracking gas concentration unit comprising about 20 mol.% ethylene and about an 80 mol.% mixture of methane, ethane, propane and hydrogen, is charged to the bottom of an absorption column 1 through line 2 at a rate to provide about 200 lb. moles of ethylene per hour. The absorption column is suitably a bubble cap, packed, or similar type column. The ethylene-containing feedstock is processed upwardly through the absorption column 1 in countercurrent contact with a liquid mixture of ethyl hydrogen sulfate and diethyl sulfate esters introduced into the top of said column from line 15 as hereinafter related. The ethylene portion of the off-gas feedstock is absorbed in the liquid ester mixture at a pressure of about 200 psig. and at a temperature maintained at about 80° C. Excess heat of absorption can be removed from the absorption column with the aid of one or more internal cooling coils 3 through which water is circulated as the coolant. The major portion of the unabsorbed nonolefinic gases is removed from the absorption column through an overhead line 4 containing a pressure control valve 5. A minor portion of said gases is recovered from the absorption column entrained in the liquid ester mixture and utilized as hereinafter described. The liquid effluent stream, recovered from the bottom of the absorption column through line 6 and a pressure reducing valve 7, provides about 1000 lb. moles of ethyl hydrogen sulfate and 1000 lb. moles of diethyl sulfate to a hydrolyzer 8 per hour.

The liquid mixed ester stream enters the hydrolyzer 8 from line 6, the hydrolyzer being operated at a temperature of about 80° C. under atmospheric pressure conditions. The hydrolyzer is shown as a horizontal vessel comprising a plurality of stages 9 defined by vertical baffles 10 and 25. The liquid mixed ester stream is processed through the hydrolyzer 8 while maintaining the liquid level generally below the top of said baffles 10, but overflowing baffles 25 so that said liquid stream progresses from stage to stage by way of openings 11 situated in the bottom of said baffles, or by overflow from alternating baffles 25. A measured amount of water, about 1000 lb. moles per hour, dispersed in a stripping gas, is charged to the hydrolyzer from line 21 and apportioned between the several stages by way of multiple lines 22. The water-containing stripping gas serves to maintain the liquid ester mixture in an agitated state while simultaneously hydrolyzing the diester contained in the mixture and stripping the ethanol hydrolysis product therefrom. The hydrolyzer is designed to facilitate the overhead recovery of ethanol from each stage, substantially immediately as formed in order to promote the equilibrium hydrolysis reaction in the next succeeding stage, and to discourage the formation of ether by-products. The ethanol hydrolysis product is collected with the stripping gases in the upper portion of the hydrolyzer 8 and withdrawn through an overhead line 12, about 200 lb. moles of ethanol being withdrawn per hour.

A liquid hydrolyzer effluent stream comprising about 1200 lb. moles of ethyl hydrogen sulfate and 800 lb. moles of diethyl sulfate per hour is recovered through line 13 and recycled by means of pump 14, and introduced by way of line 15 into the top of the absorption column 1 as heretofore mentioned. Line 26 is provided for the withdrawal and separation of polymeric materials—oils and tars—by means not shown.

The overhead effluent from the hydrolyzer is passed through a heat exchanger 16 and deposited in a separator 17. A crude ethanol product is settled out and recovered from the separator via line 18, and this crude product is further treated for the separation of ether by-products and ethanol purification by conventional means which are not shown. Stripping gas, including the residual non-olefinic gases recovered from the absorption column 1 entrained in the liquid mixed ester effluent, is recovered from the separator through an overhead line 19. Excess stripping gas is vented through a control valve 20, and the balance is recycled to the hydrolyzer 8 by way of line 21 and multiple lines 22, and by means of a recycle compressor 23. Make-up water or steam is introduced into the recycle stream from line 24.

The improved indirect hydration process described in the foregoing specification substantially limits the corrosion associated with the repeated dilution and reconcentration of sulfuric acid as heretofore practiced. Further, the high heat load heretofore required for the acid reconcentration, and the costly equipment essential thereto, is substantially eliminated; and the utilities demand relating to the separation of water from the crude alcohol is markedly reduced.

I claim as my invention:

1. A process for the manufacture of a $C_2$–$C_5$ alcohol which comprises the steps of:
   (a) treating a $C_2$–$C_5$ olefin in an absorption zone in admixture with a $C_2$–$C_5$ alkyl hydrogen sulfate at conditions to form a $C_2$–$C_5$ dialkyl sulfate;
   (b) treating said dialkyl sulfate in a hydrolyzing zone in admixture with a measured amount of water at conditions effecting the partial hydrolysis of said dialkyl sulfate and the formulation of a $C_2$–$C_5$ alkyl hydrogen sulfate and a $C_2$–$C_5$ alcohol;
   (c) separating said alcohol; and,
   (d) recycling the alkyl hydrogen sulfate to said absorption zone and treating said $C_2$–$C_5$ olefin in admixture therewith in accordance with step (a).

2. The process of claim 1 further characterized in that $C_2$–$C_5$ olefin is ethylene, said $C_2$–$C_5$ alcohol is ethanol, said $C_2$–$C_5$ alkyl hydrogen sulfate is ethyl hydrogen sulfate, and said $C_2$–$C_5$ dialkyl sulfate is diethyl sulfate.

3. The process of claim 1 further characterized with respect to step (a) in that said conditions include a temperature of from about 60° to about 100° C. and a pressure of from about 100 to about 500 psig.

4. The process of claim 1 further characterized with respect to step (a) in that said conditions include a temperature of from about 70° to about 80° C. and a pressure of from about 200 to about 350 psig.

5. The process of claim 1 further characterized with respect to step (a) in that said olefin is admixed with said alkyl hydrogen sulfate in a mole ratio of from about 0.1:1 to about 1:1.

6. The process of claim 1 further characterized with respect to step (b) in that said conditions include a temperature of from about 50° to about 90° C.

7. The process of claim 1 further characterized with respect to step (b) in that said conditions include a multiple stage hydrolysis of said dialkyl sulfate with the separation of said alcohol from each stage substantially immediately as formed.

8. The process of claim 1 further characterized with respect to step (b) in that said dialkyl sulfate is treated serially in a multiple stage hydrolyzing zone in admixture with a measured amount of water, the water concentration in each of said stages being insufficient to hydrolyze all of the diethyl sulfate contained therein to alcohol and alkyl hydrogen sulfate, a substantial portion of said alcohol being stripped from each of said stages prior to the further hydrolysis of said dialkyl sulfate in the ensuing stages.

9. The process of claim 1 further characterized with respect to step (d) in that unreacted dialkyl sulfate is recycled to said absorption zone in admixture with said alkyl hydrogen sulfate.

* * * * *